(12) United States Patent
Benjamin (10) Patent No.: US 11,401,222 B2
(45) Date of Patent: Aug. 2, 2022

(54) METHOD FOR RECOVERY OF PARAXYLENE WITH REDUCED CRYSTALLIZATION LOAD

(71) Applicant: Ineos US Chemicals Company, Naperville, IL (US)

(72) Inventor: Brian Benjamin, Chicago, IL (US)

(73) Assignee: INEOS US CHEMICALS COMPANY, Naperville, IL (US)

( * ) Notice: Subject to any disclaimer, the term of this patent is extended or adjusted under 35 U.S.C. 154(b) by 60 days.

(21) Appl. No.: 16/769,197

(22) PCT Filed: Dec. 5, 2018

(86) PCT No.: PCT/US2018/064081
§ 371 (c)(1),
(2) Date: Jun. 2, 2020

(87) PCT Pub. No.: WO2019/113218
PCT Pub. Date: Jun. 13, 2019

(65) Prior Publication Data
US 2021/0371359 A1    Dec. 2, 2021

Related U.S. Application Data

(60) Provisional application No. 62/594,926, filed on Dec. 5, 2017.

(51) Int. Cl.
| | |
|---|---|
| *C07C 7/00* | (2006.01) |
| *B01D 3/14* | (2006.01) |
| *B01D 9/00* | (2006.01) |
| *B01D 53/047* | (2006.01) |
| *C07C 5/27* | (2006.01) |
| *C07C 7/12* | (2006.01) |
| *C07C 7/14* | (2006.01) |

(52) U.S. Cl.
CPC .............. *C07C 7/005* (2013.01); *B01D 3/143* (2013.01); *B01D 9/0004* (2013.01); *B01D 53/047* (2013.01); *C07C 5/277* (2013.01); *C07C 7/12* (2013.01); *C07C 7/14* (2013.01); *B01D 2009/0086* (2013.01); *B01D 2253/116* (2013.01); *B01D 2257/7027* (2013.01)

(58) Field of Classification Search
CPC .... C07C 7/00; C07C 7/09; C07C 7/04; C07C 7/12; C07C 7/14; C07C 5/27; B01D 3/14; B01D 9/00; B01D 53/047
See application file for complete search history.

(56) References Cited

FOREIGN PATENT DOCUMENTS

| WO | 2001/062691 | 8/2001 | |
|---|---|---|---|
| WO | 2002/004391 | 1/2002 | |
| WO | WO-0204391 A1 * | 1/2002 | ............. C07C 7/005 |

OTHER PUBLICATIONS

The International Search Report (ISR) with Written Opinion for PCT/US2018/064081 dated Mar. 28, 2019, pp. 1-10.

* cited by examiner

*Primary Examiner* — Youngsul Jeong
(74) *Attorney, Agent, or Firm* — McDonnell, Boehnen, Hulbert & Berghoff LLP (57) ABSTRACT

A method for the recovery paraxylene with reduced crystallization. Paraxylene is recovered from a mixture of C8 aromatic hydrocarbons in a pressure swing adsorption zone and a crystallization zone. The invention provides for lower throughput through the crystallization zone, resulting in lower capital costs, reduced electricity in operating separation equipment, as well as reduced refrigeration duty.

10 Claims, 4 Drawing Sheets

METHOD FOR RECOVERY OF PARAXYLENE WITH REDUCED CRYSTALLIZATION LOAD

The present teachings relate generally to processes for recovering paraxylene, and in particular, to processes utilizing pressure swing adsorption for recovering paraxylene.

BACKGROUND

Paraxylene is a chemical intermediate that is oxidized to form terephthalic acid, which is a precursor to polyester.

Paraxylene is typically manufactured and recovered from streams comprising "mixed xylenes." In the industry, mixed xylenes refer to a narrow boiling distillation heart cut of C8 aromatic hydrocarbons comprising the three xylene isomers orthoxylene, metaxylene, and paraxylene, as well as the structural isomer ethylbenzene. Mixed xylenes may also contain non-aromatic compounds with boiling points close to the xylenes. These mainly comprise C9 paraffins and naphthenes. Mixed xylenes generally also contain low levels of toluene and C9 and higher aromatics present due to their imperfect separation in the distillation towers used to produce the mixed xylenes heart cut. Mixed xylenes are typically obtained from a reformate of the refinery catalytic reformer unit or another unit used to produced mixed xylenes, such as a non-selective toluene disproportionation (TDP) unit, a selective toluene disproportionation (STDP) unit, a non-selective or selective toluene alkylation unit, a toluene/aromatic C9-plus transalkylation (TA) unit or an aromatic C9-plus transalkylation unit.

Paraxylene manufacturing units typically have three sections in a recycle loop: 1) a reaction section comprising a xylene isomerization catalyst and an ethylbenzene conversion catalyst; and 2) a fractionation section for separating byproducts produced in the reaction section and/or present in the fresh feed; and a 3) a paraxylene recovery section for recovering paraxylene from a mixture of xylene isomers and ethylbenzne. A recycle returns a paraxylene-lean stream formed as a reject filtrate in the paraxylene recovery section to the reaction section.

The isomerization catalyst returns a paraxylene-lean stream to its near equilibrium ratio of 1:2:1 (paraxylene:metaxylene:orthoxylene). The ethylbenzene conversion catalyst is also present because it is not practical to remove ethylbeneze by distillation because its boiling point is very close to the xylene isomers. Thus, ethylbenzene must be converted to xylenes or to byproducts that can be easily separated by distillation to prevent its build-up in the loop. For example, ethylbenzene isomerization-type catalysts (also known as naphthene pool catalysts) have the ability to convert a portion of the ethylbenzene to xylene isomers via C8 naphthene intermediates. Ethylbenzene dealkylation-type catalysts convert ethylbenzene primarily via reaction with hydrogen to form benzene and ethane. Ethylbenzene transalkylation-type catalysts convert ethylbenzene primarily by the transfer of the ethyl group to another ethyl benzene or to a xylene.

All of these catalysts produce by-products from the ethylbenzene conversion reactions and/or side reactions that must be separated in the fractionation section. These by-products include benzene, toluene, and C9-plus aromatics. The fractionation zone also removes C9-plus aromatics and other heavies present in the feed.

Two known methods for recovering paraxylene in the paraxylene recovery section are crystallization and selective adsorption. Selective adsorption processes include the UOP Parex process described in R A Meyers (editor) Handbook of Petroleum Refining Processes, Third Edition (2004) and the Axens Eluxyl process described in G Ash, et al, Oil and Gas Technology, 49 (5), 541-549 (2004). However, crystallization is often preferred to selective adsorption because it leads to overall process energy savings. Although xylene isomers and ethylbenzene have undesirably similar boiling points (making distillation difficult), they have dramatically different melting points. Pure paraxylene freezes at 56° F. (13° C.), pure metaxylene freezes at −54° F. (−48° C.), pure orthoxylene freezes at −13° F. (−25° C.) and pure ethylbenzene freezes at −139° F. (−95° C.).

In a typical crystallization zone for recovering paraxylene, liquid paraxylene is crystallized from a feedstream comprising the xylene isomers and ethylbenzene. The paraxylene is generally caused to crystallize by cooling the feedstream to a temperature below the freezing point of the paraxylene but preferably above the freezing point of the other components in the feedstream. More particularly, the temperature is selected to seek to optimize the crystallization of paraxylene, for example by selecting a temperature at which paraxylene freezes but which is above the eutectic temperature (the eutectic temperature is the temperature at which a xylene isomer other than paraxylene begins to co-crystallize). The paraxylene-metaxylene and paraxylene-orthoxylene eutectic temperatures can be close depending on the composition within the crystallizer, so either metaxylene or orthoxylene may be the first isomer to begin to co-crystallize. For non-selective feedstocks, the eutectic temperature is typically around −88° F. (−67° C.) to around −94° F. (−70° C.).

The low temperatures required to crystallize paraxylene from xylene mixtures are typically achieved by a cascaded vapour compression refrigerant system using a Deep Refrigerant. A Deep Refrigerant is defined as one for which it is generally not possible, or not economic, to compress its vapour or gas to a pressure level where it can be condensed by air or water cooling. Ethylene is a Deep Refrigerant, because its critical temperature is 49° F. (9.5° C.), and its critical pressure is 50.76 bar. Thus, for most places on earth, for at least part of the year, ethylene is a gas above its critical temperature at ambient temperature, and it is not possible to condense ethylene via air or water cooling. When used as a refrigerant, ethylene is usually condensed by transferring heat to a High Level Refrigerant. A High Level Refrigerant is defined as one for which it is possible to condense its vapour against air or water. Thus, a cascaded ethylene/propylene, ethylene/propane, or ethylene/ammonia refrigeration system can be used to achieve the low temperatures required for paraxylene crystallization.

Effluent from the crystallization zone contains paraxylene solids dispersed in a mother liquor, and it will typically therefore be necessary to separate these solids in one or more solid-liquid separation devices, such as centrifuges. Separation of the effluent produces a filtrate and a relatively paraxylene-rich cake. The cake obtained by separating the effluent from the crystallization stage contains paraxylene crystals with adhered mother liquor that contains ethylbenzene, other xylene isomers, unrecovered paraxylene and other components of the feedstream. To improve the purity, the cake is typically further processed in one or more reslurry zones in which the cake is equilibrated with a diluent stream comprising liquid paraxylene to provide a slurry. The reslurry effluent is separated in a solid-liquid separator to form a relatively pure paraxylene solid product and a filtrate that may be recycled or used in other parts of the process.

Another method for recovering paraxylene from mixed xylenes is known as pressure swing adsorption and is disclosed, for example, in U.S. Pat. Nos. 6,573,418, 6,600,083, 6,627,783, 6,689,929, and 7,271,305. In a pressure swing adsorption unit, a vapor phase containing mixed xylenes is fed at elevated temperature and pressure to a bed of fixed adsorbent containing a selective molecular sieve. Paraxylene and ethylbenzene are preferentially adsorbed to the sieve. The remaining stream is rich in metaxylene and orthoxylene and passes out of the pressure swing adsorption unit. The pressure is then lowered and paraxylene and ethylbenzene are desorbed to form a paraxylene and ethylbenzene rich effluent stream. This effluent may be then sent to a crystallization zone for recovery of the paraxylene.

While prior techniques have provided effective processes for recovering high purity paraxylene, there remains a need to continue to reduce variable and capital cost of the paraxylene manufacturing process.

SUMMARY

According to one aspect of the invention, a process for recovering paraxylene is provided. A C8-rich aromatic hydrocarbon mixture is separated in a pressure swing adsorption zone to form a first paraxylene-rich stream and a first paraxylene-lean stream. At least a portion of the first paraxylene-rich stream is separated in a crystallization zone to form a paraxylene-rich product stream and a second paraxylene-lean stream. The ratio of the total mass of the first paraxylene-rich stream to the total mass of the paraxylene-rich product stream is less than 6. At least a portion of second paraxylene-lean stream is isomerized to form an isomerate having a paraxylene concentration greater than the paraxylene concentration of the second paraxylene-lean stream. At least a portion of the isomerate is used to form the C8-rich aromatic hydrocarbon mixture.

According to another aspect of the invention, a process for the recovery of a paraxylene product from a mixture of C8 aromatic hydrocarbons is provided. A C8-rich aromatic hydrocarbon mixture is separated in a pressure swing adsorption zone to form a first paraxylene-rich stream and a first paraxylene-lean stream. At least a portion of the first paraxylene-rich stream is separated in a crystallization zone to form a paraxylene-rich product stream and a second paraxylene-lean stream. The ratio of the total mass of the second paraxylene-lean stream to the total mass of the paraxylene-rich product stream is less than 5. At least a portion of second paraxylene-lean stream is isomerized to form an isomerate having a paraxylene concentration greater than the paraxylene concentration of the second paraxylene-lean stream. At least a portion of the isomerate is used to form the C8-rich aromatic hydrocarbon mixture.

Other aspects of the invention will be apparent to those skilled in the art in view of the description that follows.

DETAILED DESCRIPTION

By way of general introduction, a process for recovering paraxylene is provided. The invention provides for lower throughput through the crystallization zone, resulting in lower capital costs, reduced electricity in operating separation equipment, as well as reduced refrigeration duty.

Figure 1A:
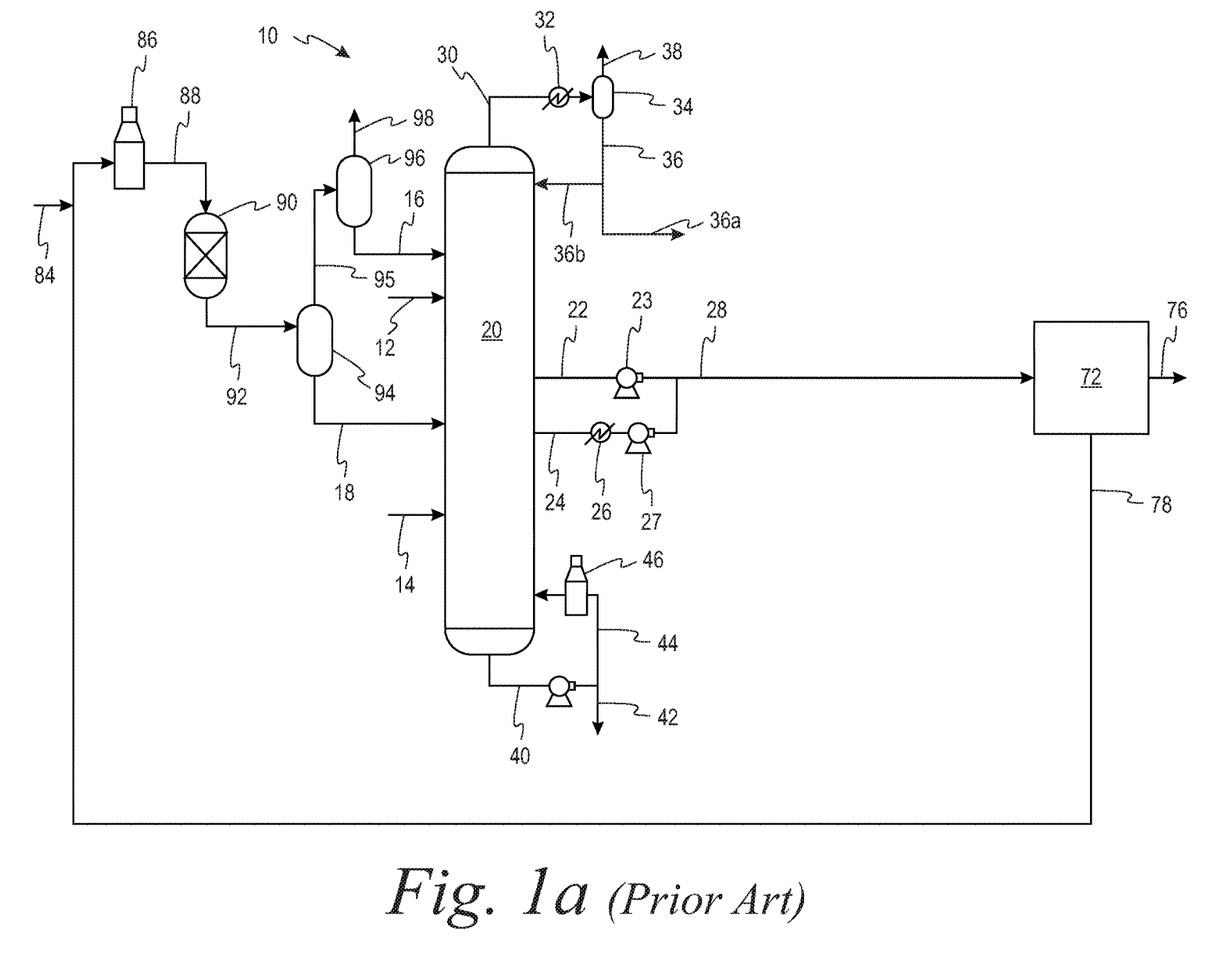
FIG. 1a shows a process flow diagram for manufacturing paraxylene according to one prior art method.
Figure 1B:
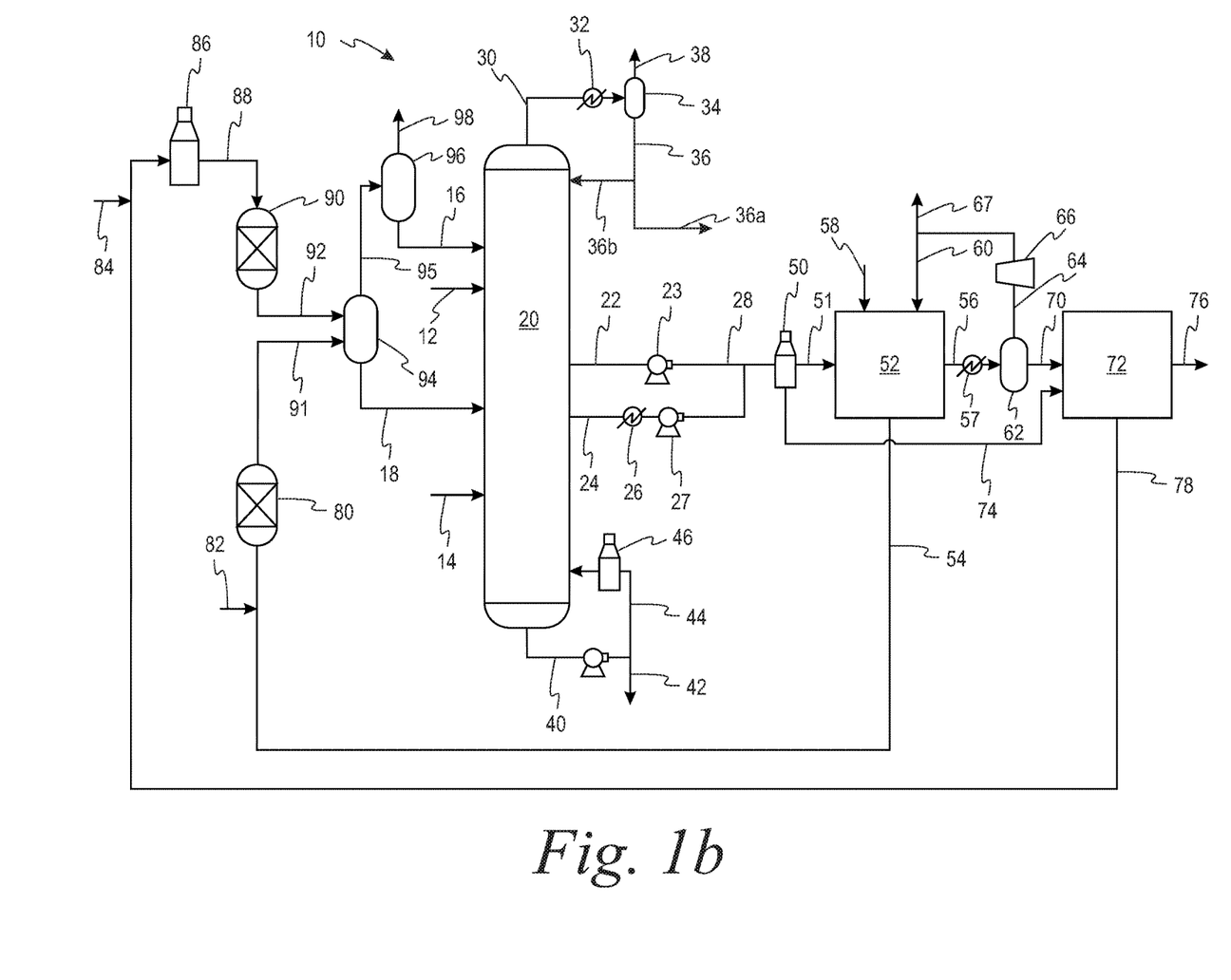
FIG. 1b shows a process flow diagram for manufacturing paraxylene in accordance with one embodiment of the present invention.

Referring now to FIG. 1a and FIG. 1b, a process for the recovery of paraxylene product is shown generally at 10. FIG. 1a illustrates a prior art process for manufacturing paraxylene, and FIG. 1b illustrates a process in accordance with the present invention. A fresh feed 12 including mixed xylenes is fed to a fractionation zone including a xylene recovery distillation column 20 for separation of C8-rich aromatic hydrocarbon mixture from other components. In one embodiment, the mixed xylene fresh feed comprises paraxylene, orthoxylene, metaxylene, as well as the structural isomer ethylbenzene. In other embodiments, the fresh feed also comprises C7 and C9+ aromatic compounds, as well as non-aromatic compounds such as C9 paraffins and naphthenes. Typically, the mixed xylene fresh feed 12 is formed as reformate of a refinery catalytic reformer unit, or another unit used to produced mixed xylenes, such as a non-selective toluene disproportionation (TDP) unit, a selective toluene disproportionation (STDP) unit, a non-selective or selective toluene alkylation unit, a toluene/aromatic C9-plus transalkylation (TA) unit or an aromatic C9-plus transalkylation unit. The mixed xylene fresh feed 12 is typically at least 90 wt % mixed xylenes. In some embodiments, the mixed xylene fresh feed 12 is at least 95 wt %, 98 wt %, or 99 wt % mixed xylenes.

In some embodiments, a second fresh feed mixed xylene containing stream 14 is also fed the column 20. The second mixed xylene containing stream 14 is typically a heavier cut of reformate containing a higher concentrations of C9+ compounds, and is fed lower on the column 20 than the first fresh feed 12. The second mixed xylene stream 14 typically contains at least 10 wt % of C9+ compounds. In some embodiments, the mixed xylene fresh feed 12 is at least 15 wt %, 20 wt %, 25 wt %, 35 wt %, or 50 wt % of C9+ compounds.

At least one other xylene containing stream resulting from recycle loops in the process 10 is fed to the column 20. In the embodiment shown, two such feeds 16, 18 are shown. Those skilled in the art will appreciate that other configurations of the recycled feed are also possible. The xylene containing feed stream 16 and xylene containing feed stream 18 typically contain proportionally less ethylbenzene than the mixed xylene feed streams 12, 14. The feed streams 16 and 18 further comprise benzene. In some embodiments, the feed streams contain at least 1 wt % or 2 wt % benzene. In other embodiments, feed stream 16 contains at least 5 wt % benzene.

The xylene recovery column 20 is configured to separate the feed streams 12, 14, 16, 18 into one or more streams comprising a C8-rich aromatic hydrocarbon mixture, a stream containing C7− compounds, and a stream containing C9+ compounds. In the embodiment shown in FIG. 1a or FIG. 1b, a first sidedraw stream 22 comprises a liquid phase C8-rich aromatic hydrocarbon mixture, while a second sidedraw stream 24 comprising a vapor phase C8-rich aromatic hydrocarbon mixture. The first sidedraw stream 22 is withdrawn at location on the column above the second sidedraw stream 24. The feed stream 18 is introduced to the column above the vapor phase sidedraw stream 24 so that gaseous components in the feed stream 18 do not exit through the vapor phase sidedraw stream 24. The liquid phase sidedraw phase is pressurized by pump 23. The vapor phase sidedraw stream is condensed by condenser 26 and the resulting condensate is pressured by pump 27. The pressurized condensate of the vapor phase sidedraw stream and the pressurized liquid phase sidedraw stream are combined to form a combined C8-rich aromatic hydrocarbon mixture stream 28.

An overhead product stream 30 is withdrawn from the top of the column 20 and comprises C7− compounds including benzene, toluene, and ethane. The overhead product stream 30 is partially condensed by condenser 32 and the condenser effluent is separated into liquid and gaseous components in flash drum 34. The liquid phase is partially returned to the column 30 as a reflux stream 36b and partially removed from the process via stream 36a. The gaseous components are removed from the process as a light co-product stream 38.

A bottoms product stream 40 is removed from the bottom of the column and comprises C9+ compounds including trimethylbenzene and methylethylbenzene. A portion of the bottoms product is recovered as a bottoms co-product stream 42, while another portion 44 of the bottoms product stream 40 is reboiled by reboiler furnace 46 and returned to the column 20. The reboiler furnace 46 provides for the elevated temperature of the column 20 which operates in a temperature gradient, for example, between 500° F. (260° C.) and 50° F. (10° C.) and a pressure of 15-80 psia.

In the prior art process shown in FIG. 1a, the combined C8-rich aromatic hydrocarbon mixture stream 28 is fed to a paraxylene recovery zone 72. However, in the present invention illustrated in FIG. 1b, at least a portion of the C8-rich aromatic hydrocarbon mixture 28 recovered from the fractionation zone is pre-heated by furnace 50 and one or more heat exchangers (not shown) and delivered to a pressure swing adsorption zone 52. In the pressure swing adsorption zone 52, the C8-rich aromatic hydrocarbon mixture is fed at elevated temperature and pressure to a bed of fixed adsorbent containing a selective molecular sieve. Paraxylene and ethylbenzene are preferentially adsorbed to the sieve. The remaining stream is rich in metaxylene and orthoxylene and passes out of the pressure swing adsorption unit as paraxylene-lean stream 54. The partial pressure is then lowered and paraxylene and ethylbenzene are desorbed to form a paraxylene-rich and ethylbenzene-rich effluent stream 56. The configuration and operation of the pressure swing adsorption zone is more fully described below and in reference to FIG. 2.

A first source of pressurized hydrogen purge gas 58 is fed to the pressure swing adsorption zone 52. A second source of hydrogen purge gas 60 is formed condensing the paraxylene-rich and ethylbenzene-rich effluent stream 56 in condenser 57 and then flashing in drum 62 to remove hydrogen. The resulting hydrogen-rich stream 64 is compressed by compressor 66 and the resulting pressured hydrogen-rich stream is a second source of hydrogen purge gas 60 that is fed to the pressure swing adsorption unit 52. In one embodiment, the first hydrogen purge gas 58 is at a higher pressure than the second hydrogen purge gas 60. In one embodiment, the first hydrogen purge gas 58 is introduced at a pressure between 200 and 400 psia, and the second hydrogen purge is introduced at a pressure between 40 and 100 psia. In another embodiment, the first hydrogen purge is within 50 psi of the adsorption pressure of the paraxylene in the zone and the second hydrogen purge is within 50 psi of the desorption pressure of the paraxylene. Typically, the adsorption pressure will be in the range of 175 psia to 375 psia and the desorption pressure will be in the range of 30 psia to 90 psia. By maintaining a desorption pressure above ambient, the paraxylene-rich and ethylbenze-rich effluent 56 may be maintained at temperature high enough to allow useful amounts of heat to be recovered in condenser 57. In one embodiment, the temperature of the effluent 56 entering the condenser 57 is between 150° F. (65.6° C.) and 400° F. (204.4° C.).

The paraxylene-rich and ethylbenzene-rich effluent 70 exiting the flash drum 62 is fed to a paraxylene recovery zone 72. In one embodiment, a C8-rich aromatic hydrocarbon mixture feed 74 to the paraxylene recovery zone 72 comprises a second portion of the combined C8-rich aromatic hydrocarbon mixture stream 28 exiting the column 20 and bypasses the pressure swing adsorption unit 52. In one embodiment, the second feed 74 comprises at least 10 wt % of the combined paraxylene-rich and ethylbenzene-rich stream 28. In other embodiments, the second feed 74 comprises at least 20 wt %, at least 30 wt %, at least 40 wt %, at least 50 wt %, at least 60 wt %, at least 70 wt %, at least 80 wt %, or at least 90 wt % of the combined C8-rich aromatic hydrocarbon mixture stream 28.

The paraxylene recovery zone 72 operates to produce a paraxylene product 76 and to recycle a paraxylene-lean stream 78 for further processing. In one embodiment, the paraxylene recovery zone 72 is configured to recover paraxylene product through a selective adsorption process. In another embodiment, the paraxylene recovery zone 72 is configured is configured as to recover paraxylene through a crystallization process. One particular crystallization process is described below in reference to FIG. 3.

The paraxylene-lean stream 54 exiting the pressure swing adsorption unit 52 is fed to a isomerization reactor 80. The isomerization reactor 80 is a packed bed reactor containing a bed of an isomerization catalyst for converting metaxylene and orthoxylene to paraxylene at an approximately equilibrium ratio of 1:2:1 (paraxylene:metaxylene:orthxylene). In one embodiment, hydrogen 82 is added to the paraxylene-lean stream 54 upstream of the isomerization reactor 80. In another embodiment, the paraxylene-lean 54 contains enough hydrogen after exiting the pressure swing adsorption unit 52 that make-up hydrogen is not added to the feed 54.

The second paraxylene-lean stream 78 exiting the paraxylene recovery zone 72 is mixed with fresh hydrogen 84 and pre-heated with a furnace 86 and/or one or more heat exchangers (not shown). The preheated mixture 88 is fed to the additional isomerization reactor 90. The isomerization reactor 90 contains a isomerization catalyst for converting metaxylene and orthoxylene to paraxylene at an approximately equilibrium ratio of 1:2:1 (paraxylene:metaxylene:orthxylene). In some embodiments, the isomerization reactor 90 also contains an ethylbenzene conversion, catalyst such as dealkylation catalyst for converting ethylbenzene to benzene and ethane. Suitable isomerization catalysts and ethylbenzene catalysts are disclosed, for example, in U.S. Pat. Nos. Re 31,782, 4,899,011, and 6,518,472.

In the embodiment shown, the isomerate stream 91 from the isomerization reactor 80 and the isomerate stream 92 from the additional isomerization reactor 90 are fed to a high temperature separator 94 where the streams are mixed and flashed. A liquid-rich phase bottom stream from the high temperature separator 94 is one of the xylene containing feed stream 18 to the column 20. A vapor-rich phase stream 95 exiting high temperature separator 94 is sent to a low temperature separator 96 where the vapor-rich phase stream is flashed. A liquid-rich phase stream exiting the low temperature separator 96 is another of the xylene containing feed stream 16 fed to the column. A vapor phase stream 98 exiting the low temperature separator 96 comprises hydrogen, ethane, and other light components and may be recycled and used as a source for streams 84 and/or 58 or be used for fuel.

Figure 2:
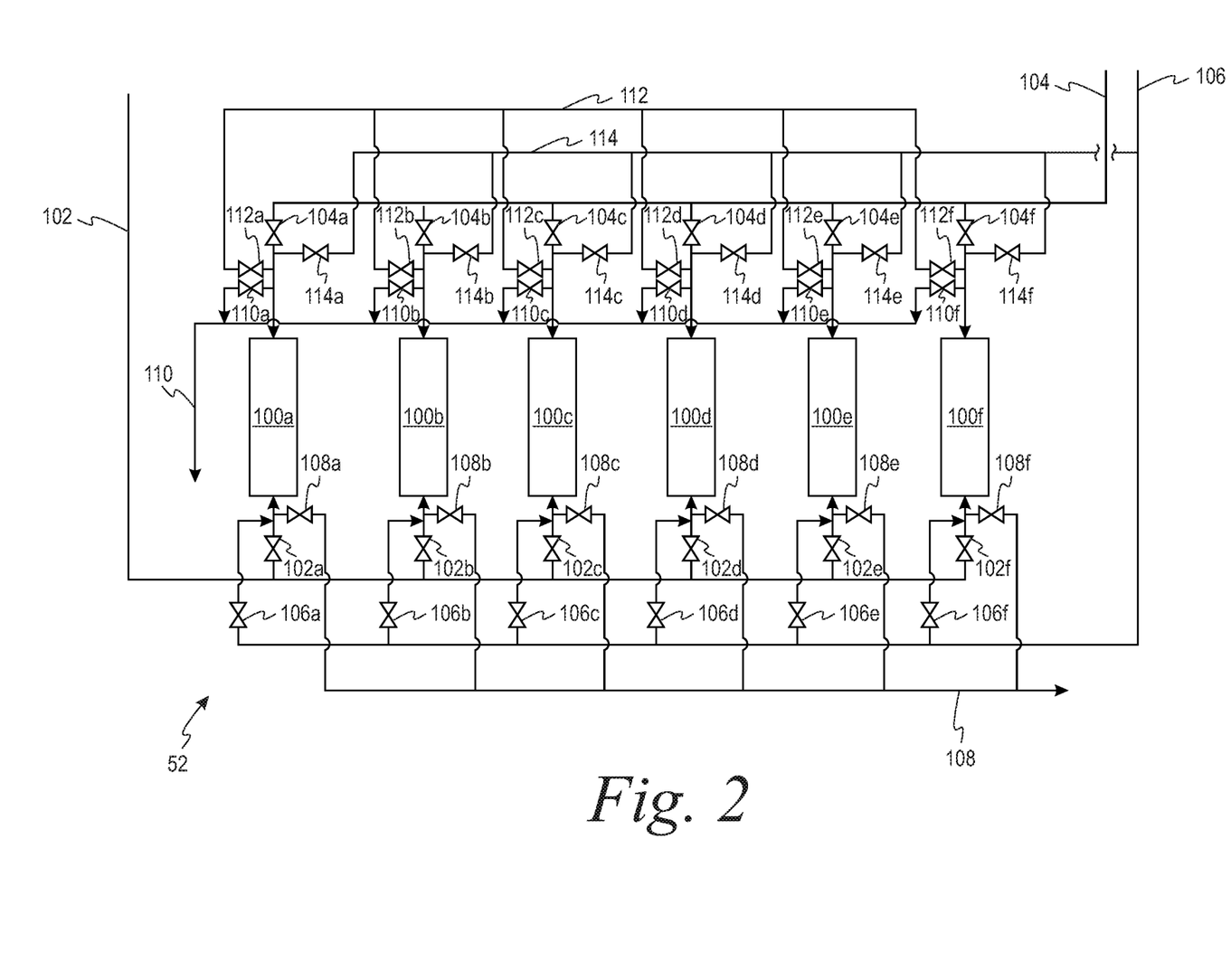
FIG. 2 shows a process flow diagram of a pressure swing adsorption zone in accordance with one embodiment of the present invention.

FIG. 2 shows one embodiment of the pressure swing adsorption zone 52 according to the present invention. The pressure swing adsorption zone 52 comprises one or more vessels 100a, 100b, 100c, 100d, 100e, 100f containing a paraxylene selective adsorbent. In the embodiment shown, there are six vessels, but those skilled in the art will recognize that other configurations are also possible, such as configurations with different numbers of vessels, e.g. 3 vessels, 4 vessels, 5 vessels, 7 vessels, 8 vessels, etc. In one embodiment, the paraxylene selective adsorbent is a non-acidic, medium pore, molecular sieve. In one embodiment, the molecular sieve is of the MFI structure type and the process is operated in the vapor phase at elevated temperatures and pressures wherein the temperature is substantially isothermal. Adsorbents useful in the present invention are based on molecular sieves that selectively adsorb paraxylene within the channels and pores of the molecular sieve while not effectively adsorbing metaxylene and orthoxylene $C_8$ isomers (i.e., total exclusion of the larger metaxylene and orthoxylene or having much slower adsorption rates compared to paraxylene).

Molecular sieves are ordered porous crystalline materials, typically formed from silica, alumina, and phosphorus oxide ($PO_4$) tetrahedra, that contain a crystalline structure with cavities interconnected by channels. The cavities and channels within the crystalline structure are uniform in size and may permit selective separation of hydrocarbons based upon molecular dimensions. Generally, the term "molecular sieve" includes a wide variety of natural and synthetic crystalline porous materials which typically are based on silica tetrahedra in combination with other tetrahedral oxide materials such as aluminum, boron, titanium, iron, gallium, and the like. In these structures networks of silicon and elements such as aluminum are cross-linked through sharing of oxygen atoms. Substitution of elements such as aluminum or boron for silicon in the molecular sieve structure produces a negative framework charge which must be balanced with positive ions such as alkali metal, alkaline earth metal, ammonium or hydrogen. Molecular sieve structures also may be formed based on phosphates in combination with other tetrahedrally substituted elements such as aluminum.

Adsorbents useful in this invention should not possess catalytic isomerization or conversion activity with respect to the C8 aromatic feedstream. Thus, suitable molecular sieves should be non-acidic. If an element such as aluminum or gallium is substituted in the molecular sieve framework, the sieve should be exchanged with a non-acidic counter-ion, such as sodium, to create a non-acidic sieve adsorbent.

Examples of molecular sieves suitable as adsorbents useful in this invention include zeolitic materials containing pore dimensions in the range of 5 to 6 angstroms ($10^{-8}$ meter), typically 5.1 to 5.7 angstroms, and preferably 5.3 to 5.6 angstroms, as measured in cross axes of the pore. This range typically is referred to as "medium pore" and typically contains 10-ring tetrahedra structures. Typical examples of medium pore molecular sieves include those with MFI and MEL framework structures as classified in Meier and Olson, "Atlas of Zeolite Structure Types," International Zeolite Association (1987), incorporated herein by reference in its entirety. A small pore molecular sieve, such as A zeolite, which contains 8-ring structures does not have a sufficiently large pore opening to effectively adsorb paraxylene within the sieve. Most large pore molecular sieves, such as mordenite, Beta, LTL, or Y zeolite, that contain 12-ring structures do not adsorb para-xylene selectively with respect to ortho- and meta-xylenes. However, several 12 ring structures, having a smaller effective pore size, for example due to puckering, are potentially useful in the invention, such as structure types MTW (e.g., ZSM-12) and ATO (e.g., ALPO-31).

Specific examples of molecular sieves include ZSM-5 (MFI structure type) and ZSM-11 (MEL structure type) and related isotypic structures. Since suitable adsorbents should not be catalytically reactive to components in the feedstream, the preferable adsorbent useful in this invention is silicalite (MFI structure type), an essentially all silica molecular sieve, which contains minimal amounts of aluminum or other substituted elements. Typically, the silica/alumina ratio of suitable silicalite is above 200 and may range above 1000 depending on the contaminant level of aluminum used in the sieve's preparation. Other MFI and MEL sieves may be use to the extent they are made non-catalytically active. Other potentially useful adsorbents include structure types MTU, FER EUO, MFS, TON, AEL, ATO, NES, and others with similar pore sizes.

A molecular sieve which is not catalytically reactive will typically exhibit less than 10% conversion of paraxylene to metaxylene and orthoxylene, and in some embodiments, less than 5%, and in other embodiments less than 1%, at the temperature of operation for the process of the invention.

The C8-rich aromatic hydrocarbon mixture enters pressure swing adsorption zone 52 through xylene header 102 and is introduced into vessels 100a, 100b, 100c, 100d, 100e, 100f through respective feed control valves 102a, 102b, 102c, 102d, 102e, 102f. The first hydrogen purge 58 enters the vessels 100a, 100b, 100c, 100d, 100e, 100f through high pressure hydrogen header 106 and high pressure hydrogen feed control valves 106a, 106b, 106c, 106d, 106e, 106f, respectively. The second hydrogen purge gas 60 enters the vessels 100a, 100b, 100c, 100d, 100e, 100f through low pressure hydrogen header 104 and low pressure hydrogen feed control valves 104a, 104b, 104c, 104d, 104e, 104f, respectively.

The pressure swing adsorption zone 52 also comprises a paraxylene and ethylbenzene collection header 108 and a set of outlet control valves 108a, 108b, 108c, 108d, 108e, 108f for removing a paraxylene-rich and ethylbenzene-rich stream 56 from each of the vessels 100a, 100b, 100c, 100d, 100e, 100f, respectively. The pressure swing adsorption zone 52 also comprises a metaxylene and orthoxylene collection header 110 and a set of outlet control valves 110a, 110b, 110c, 110d, 110e, 110f for removing the first paraxylene-lean stream 54 from the vessels 100a, 100b, 100c, 100d, 100e, 100f, respectively. The pressure swing adsorption zone 52 also comprises a pressure equalization header 112 and a set of equalization control valves 112a, 112b, 112c, 112d, 112e, 112f for equalizing the pressure between two or more of the vessels 100a, 100b, 100c, 100d, 100e, 100f, respectively. The pressure swing adsorption zone 52 also comprises a hydrogen pressurization header 114 which is fed from high pressure hydrogen source 106 and a set of pressurization control valves 114a, 114b, 114c, 114d, 114e, 114f for pressurizing vessels 100a, 100b, 100c, 100d, 100e, 100f respectively.

The vessels 100a, 100b, 100c, 100d, 100e, 100f in the pressure swing adsorption zone 52 are operated in a sequence of operations, the sequence of operations in each vessel being offset in time from the sequence of operations in the other vessels such that the vessels operate together in a pseudo-continuous manner.

The sequence of operations are now described with reference to the first vessel 100a. All the valves are controlled automatically by a control system (not shown). The valves are maintained closed unless they are described as being opened below for a particular operation.

In the first operation, designated "FEED", C8-rich aromatic hydrocarbon stream is introduced through feed header 102 and feed control valve 102a to vessel 100a at elevated pressure. The paraxylene and ethylbenzene molecules adsorb to the adsorbent, while the metaxylene and orthoxylene molecules are blown through the bed and leave the process through the outlet control valve 110a and the metaxylene and orthoxylene collection header 110.

In the second operation, designated "HPPu," (high pressure purge) the high pressure purge gas 58 (FIG. 1b) is fed through header 106 and control valve 106a to sweep the bed. This hydrogen displaces all of the metaxylene and orthoxylene left in the void space of the bed and continues to flow out through control valve 110a and header 110 after the FEED operation is complete. This allows the paraxylene and ethylbenzene to be extracted in a later operation without being contaminated by metaxylene and orthoxylene.

In the third operation, designated "E1d", (equalization #1 down) the pressure in vessel 100a is equalized with the pressure in another vessel, for example, vessel 100d, by opening valves 112a and 112d. This depressurization in vessel 100a is performed so that the paraxylene and orthoxylene can be removed, but in order to keep the hydrogen from being blown out with the paraxylene and ethylbenzene, the pressure is equalized with another vessel that is at the point in the process where it needs to start re-pressurizing to get ready for its next feed step. This saves hydrogen from being sent out of the process unnecessarily and reduces the overall hydrogen needs.

In the fourth operation, designated "E2d" (equalization #2 down), the pressure in vessel 102a is subjected to another hydrogen equalization step which takes place at a lower pressure than E1d and saves more hydrogen. For example, the pressure in vessel 102a may be equalized with the pressure in vessel 102c by opening control valve 112a and valve 112c.

In the fifth operation, designated "CnD" (Countercurrent depressurization), the bed is fully depressurized to its lowest desorption pressure and the paraxylene and ethylbenzene begin to desorb off the adsorbent and are removed through valve 108a.

In the sixth operation, designated "LPPU" (Low Pressure Purge), the low pressure hydrogen 60 (FIG. 1b) is fed through low pressure hydrogen header 104 and valve 104a into vessel 100a at the desorption pressure and sweeps the bed. This sweeping of the bed further drops the partial pressure of paraxylene and ethylbenzene. This causes further desorption of paraxylene and ethylbenzne from the adsorbent. This increases the capacity of the adsorbent such that a commercially relevant amount of paraxylene and ethylbenzene can be routed through the bed during each cycle. Without this sweep flow, the capacity would lower and the space velocities would be higher.

In the seventh operation, "E2u" (equalization #2 up), hydrogen pressure is equalized with that from another vessel, such as vessel 100e, which is simultaneously undergoing E2d, by opening valves 112a and 112e.

In the eighth operation, "E1u" (equalization #1 up), hydrogen is equalized with that from another vessel, such as vessel 100d, which is simultaneously undergoing E1d, by opening valve 112a and 112d.

In the ninth operation, "H2P" (hydrogen pressurization), the bed is brought up to the feed pressure after the two equalization up steps by fresh hydrogen by opening valve 114a.

All six vessels 100a, 100b, 100c, 100d, 100e, 100f go through this same cycle of nine operations, but at any given time, each vessel is at a different stage of the cycle. The system is designed and operated such that one of vessels is always in the FEED operation so that the feed to the pressure swing adsorption zone 52 as a whole is constant.

Table 1 illustrates one embodiment of a sequence of the nine operations for the pressure swing adsorption zone 52 in which plurality of vessels operate together in a pseudo-continuous manner. The Table illustrates twelve time periods and shows which operation is being performed in each vessel at each time period. A typical time period is from 5 seconds to about 120 seconds. Those skilled in the art will recognize that the sequence in Table 1 is exemplary and other sequences are also possible to carry out the invention.

TABLE 1

Sequence of Pressure Swing Adsorption Operations

| Time Period | Vessel a | Vessel b | Vessel c | Vessel d | Vessel e | Vessel f |
|---|---|---|---|---|---|---|
| 1 | Feed | HPPu | E1d | CnD | LPPu | E1u |
| 2 |  |  | E2d | LPPu | E2u | H2P |
| 3 | HPPu | E1d | CnD |  | E1u | Feed |
| 4 |  | E2d | LPPu | E2u | H2P |  |
| 5 | E1d | CnD |  | E1u | Feed | HPPu |
| 6 | E2d | LPPu | E2u | H2P |  |  |
| 7 | CnD |  | E1u | Feed | HPPu | E1d |
| 8 | LPPu | E2u | H2P |  |  | E2d |
| 9 |  | E1u | Feed | HPPu | E1d | CnD |
| 10 | E2u | H2P |  |  | E2d | LPPu |
| 11 | E1u | Feed | HPPu | E1d | CnD |  |
| 12 | H2P |  |  | E2d | LPPu | E2u |

Figure 3:
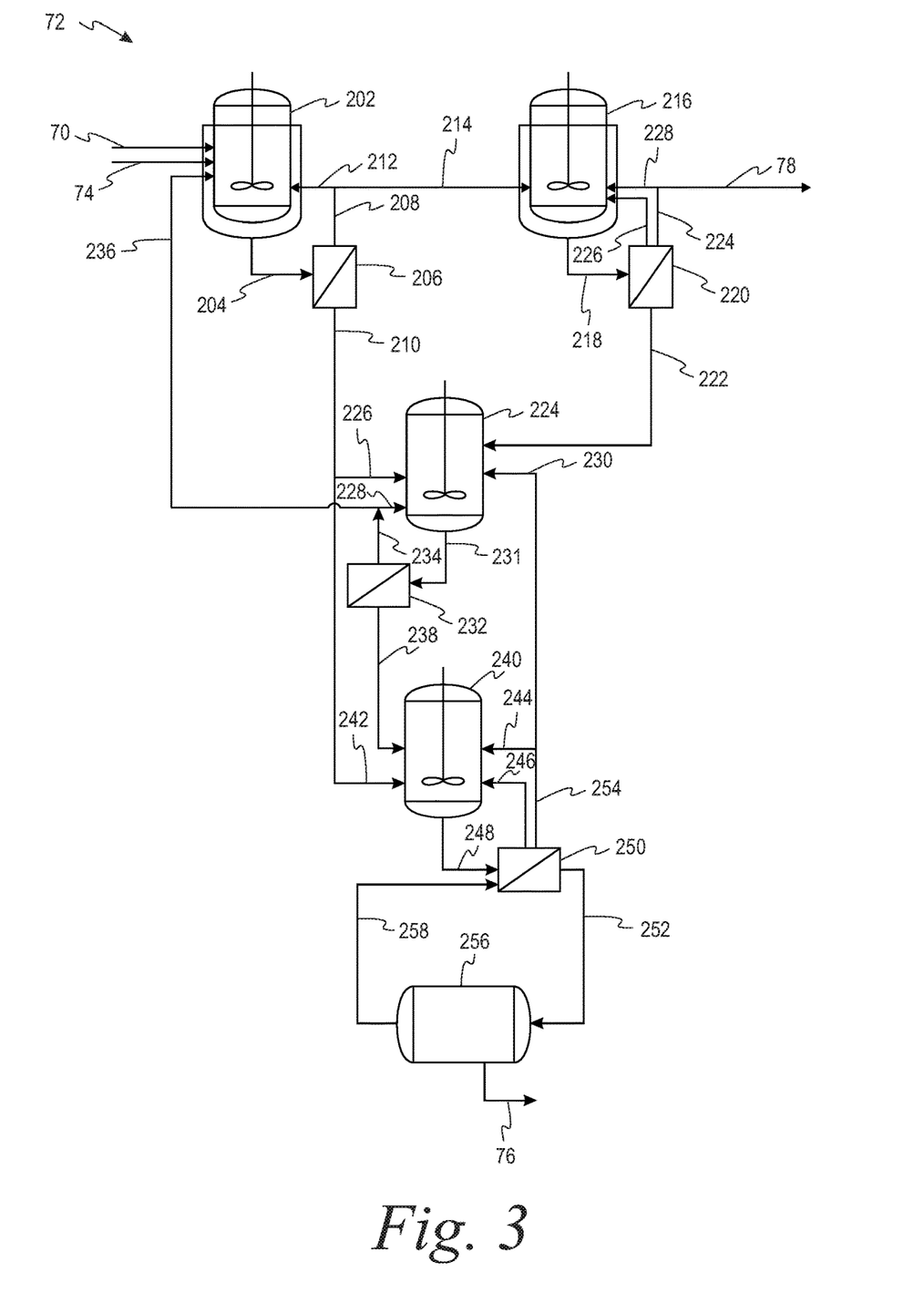
FIG. 3 shows a process flow diagram of a paraxylene recovery zone in accordance with one embodiment of the present invention.

FIG. 3 illustrates one embodiment of the paraxyene recovery zone 72 in accordance with the present invention. The paraxylene-rich and orthoxylene-rich effluent 70 enters a crystallization zone comprising a first crystallization zone comprising a first crystallizer 202 and a second crystallization zone comprising a second crystallizer 216. In one embodiment, the effluent 70 comprises at least 25 wt % paraxylene. In other embodiments, the effluent 70 comprises less than 75 wt %, less than 85 wt %, or less than 95 wt % paraxylene. The first crystallizer 202 is temperature controlled to operate to solidify paraxylene in the effluent 70. In one embodiment, the first crystallization zone operates at a temperature greater than −40° F. (−40° C.). In another embodiment, the first crystallization zone operates at a temperature greater than −30° F. (−34.4° C.). The first crystallization zone typically operates a temperature between 40° F. (4.4° C.) and −40° F. (−40° C.). The first crystallizer effluent 204 is withdrawn from the first crystallizer 202 and sent to a first solid-liquid separator 206. The first solid-liquid separator 206 separates a paraxylene-lean filtrate stream 208 from a first paraxylene-rich cake stream 210. One portion 212 of the paraxylene-lean filtrate stream may be recycled to the first crystallizer 202, while another portion 214 of the paraxylene-lean filtrate stream is sent to a second crystallizer 216. The second crystallizer 216 is temperature controlled to further solidify any remaining paraxylene. The second crystallization zone operates at a temperature less than the first crystallization zone. In one embodiment, the second crystallization zone operates at a temperature less than −70° F. (−56.7° C.). In another embodiment, the second crystallization zone operates at a temperature less than −90° F. (−67.8° C.). In another embodiment, the second crystallization zone operates at a temperature less than −110° F. (−78.9° C.). The second crystallization zone typically operates at a temperature between −30° F. (−34.4° C.) and −130° F. (−90° C.). The second crystallizer effluent 218 is withdrawn from second crystallizer 216 and introduced to a second solid-liquid separator 220. In one embodiment, the effluent 218 exiting the second crystallizer is colder than −95° F. (−70.6° C.). The second solid-liquid separator 220 separates a second paraxylene-rich cake 222 from a second paraxylene-lean filtrate stream 224. A portion 228 of the filtrate stream 224 may be recycled to the crystallizer 216, while another portion 78 of the paraxylene-lean filtrate stream 224 is recycled for further processing as described above and in reference to FIG. 1b.

The first and second solid-liquid separator 202, 216 may be any solid-liquid separation devices known in the art, such as centrifuges, rotary pressure filters, rotary vacuum filters, or filter columns. In one particular embodiment, the first solid-liquid separator 206 comprises a pusher centrifuge and the second solid-liquid separator 220 comprises a screen bowl centrifuge. In one embodiment, the second solid-liquid separator 220 removes an additional paraxylene-lean filtrate 226 before withdrawing the second paraxylene-lean filtrate 224. The additional filtrate 226 is higher in paraxylene concentration than the second paraxylene-lean filtrate 224 and is recycled to the second crystallizer 216.

The first paraxylene-rich cake 210 and the second paraxylene-rich cake 222 enters one or more reslurrying zones for removing any remaining impurities. The embodiment of FIG. 3 shows two reslurrying zones, each having a reslurry drum 224, 240. The paraxylene-rich cake 210 from the first solid-liquid separator is fed to either or both of the first reslurry drum 224 and the second reslurry drum 240 through streams 226 and 242, respectively. The second paraxylene-rich cake 222 is fed to the first reslurry drum 224. The paraxylene-rich cake(s) are reslurried in the first reslurry drum 224 with reslurrying fluids to remove impurities from the paraxylene crystals and the effluent 231 from the first reslurry drum 224 is sent to the third solid-liquid separator 232. The third solid-liquid separator 232 separates the effluent 231 into a third paraxylene-rich cake 238 and a third paraxylene-lean filtrate stream 234. A portion 228 of the third paraxylene-lean filtrate stream 234 is recycled to the first reslurry drum 224 as a reslurrying fluid, and another portion 236 may be recycled to the first crystallizer 202 for further recovery of paraxylene.

The third paraxylene-rich cake 238 is fed to a second reslurry drum 240 for further reslurrying with one or more reslurrying fluids for removing impurities from the paraxylene crystals. The effluent 248 from the second reslurry drum 240 is fed to a fourth solid-liquid separator 250. The fourth solid-liquid separator 250 separates the effluent 248 into a fourth paraxylene-rich cake 252 and a fourth paraxylene-lean filtrate stream 254. A portion 244 of the fourth paraxylene-lean filtrate stream 254 is recycled to the second reslurry drum 244 as a reslurrying fluid, and another portion 230 of the fourth paraxylene-lean filtrate stream 254 may be recycled to the first reslurry drum 224 for use as a reslurrying fluid.

The third and fourth solid-liquid separator 232, 250 may be any solid-liquid separation devices known in the art, such as centrifuges, rotary pressure filters, rotary vacuum filters, or filter columns. The fourth solid-liquid separator 250 may also be a wash column. Suitable filter columns are disclosed, for example, in U.S. Pat. Nos. 7,812,206, 8,211,319, and 8,530,716, and 8,962,906, Suitable wash columns are disclosed, for example, in U.S. Pat. Nos. 4,734,102 and 4,735,781. In one particular embodiment, the third solid-liquid separator 232 comprises a pusher centrifuge and the fourth solid-liquid separator 250 comprises a pusher centrifuge. In one embodiment, the fourth solid-liquid separator 250 removes an additional paraxylene-lean filtrate 246 before withdrawing the fourth paraxylene-lean filtrate 254. The additional filtrate 246 is higher in paraxylene concentration than the fourth paraxylene-lean filtrate 254 and is recycled to the second reslurry drum 240.

The fourth paraxylene-rich cake 252 is fed to a melt drum 256. The fourth paraxylene-rich cake is completely melted and a paraxylene product stream 76 is recovered. A portion 258 of the melted paraxylene may be recycled to the fourth solid-liquid separator 250 in order to wash impurities from the cake. In one embodiment, the paraxylene product 76 is at least 99 wt % paraxylene. In other embodiment, the paraxylene product is at least 99.5 wt %, 99.6 wt %, 99.7 wt %, or 99.8 wt % paraxylene.

The use of a pressure swing adsorption zone with an additional isomerization zone allows for less total mass being fed to the paraxylene recovery zone, because a significant portion of the metaxylene and orthoxylene in the system is recycled through stream 54 (FIG. 1b). In one embodiment, the ratio of the total mass of the paraxylene-rich stream entering the paraxylene recovery zone to the total mass of the paraxylene-rich product stream is less than 6. In other embodiments, the ratio of the total mass of the paraxylene-rich stream entering the paraxylene recovery zone to the total mass of the paraxylene-rich product stream is less than 5, less than 4, less than 3, or less than 2. In other embodiments, the ratio of the total mass of the recycle stream 78 (FIG. 1b) to the total mass of the paraxylene-rich product stream 76 is less than 5, less than 3, or less than 2. The feed to the paraxylene recovery zone also contains a higher concentration of paraxylene compared to systems not having a pressure swing adsorption zone. This is because the pressure swing adsorption zone allows for paraxylene concentrations greater than the equilibrium concentration resulting from the isomerization reaction.

According to another aspect of the invention, a method for retrofitting a system for recovering paraxylene is provided. According to the retrofitting method, the pressure swing adsorption zone 52 (FIG. 1b) is added to a pre-existing system (FIG. 1a) not having a pressure swing adsorption zone. At least a first portion 51 of the combined C8-rich aromatic hydrocarbon mixture stream 28 is routed to the pressure swing adsorption zone 52 to form a paraxylene-rich intermediate stream 56 (which is flashed in drum 62 to form stream 70) before being fed to the paraxylene recovery zone 72. The retrofit method may also comprise adding the secondary isomerization zone 80 to a pre-existing system where there was no previous secondary isomerization zone 80. The retrofit method may also include adding the bypass stream 74 so that a second portion of the combined C8-rich aromatic hydrocarbon mixture stream 28 routes directly to the paraxylene recovery zone 72, bypassing the pressure swing adsorption zone 52. The amount of C8-rich aromatic hydrocarbon mixture stream bypassed through bypass stream 74 is dependent upon the throughputs of the pressure swing adsorption zone 52 and the pre-existing equipment. In one embodiment, the pre-existing equipment does not have to be re-sized as a result of the retrofit, which allows increased recovery of paraxylene without significant capital expenditures. By enriching the combined stream 28 in paraxylene prior to its delivery to the paraxylene recovery zone and adding isomerization capacity, the retrofit method allows for increased recovery of paraxylene product compared to the pre-existing system. In one embodiment, the amount of a paraxylene product recovered by the retrofitted system increases without increasing the throughput of the primary isomerization zone 90. In another embodiment, the amount of paraxylene product recovered increases without increasing the amount of hydrogen fed to the system. In another embodiment, the amount of paraxylene product recovered increases without increasing the amount of the refrigeration duty of the crystallization zone. In another embodiment, the amount of paraxylene product recovered increases without increasing the amount of the furnace duty 86 of the primary isomerization zone. In another embodiment, the amount of paraxylene product recovered increases without increasing the amount of the furnace duty 46 of the fractionation zone.

The foregoing detailed description and the accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding claim—whether independent or dependent—and that such new combinations are to be understood as forming a part of the present specification.

The invention claimed is:

1. A process for the recovery of a paraxylene product from a mixture of C8 aromatic hydrocarbons, the process comprising:
    separating a C8-rich aromatic hydrocarbon mixture in a pressure swing adsorption zone to form a first paraxylene-rich stream and a first paraxylene-lean stream, wherein the first paraxylene-rich stream comprises less than 75 wt % paraxylene;
    separating at least a portion of the first paraxylene-rich stream in a crystallization zone to form a paraxylene-rich product stream and a second paraxylene-lean stream; wherein a ratio of the total mass of the first paraxylene-rich stream to the total mass of the paraxylene-rich product stream is less than 4; and
    isomerizing at least a portion of the second paraxylene-lean stream to form an isomerate having a paraxylene concentration greater than the paraxylene concentration of the second paraxylene-lean stream; wherein at least a portion of the isomerate is used to form said C8-rich aromatic hydrocarbon mixture.

2. The process of claim 1, wherein the ratio of the total mass of the first paraxylene-rich stream to the total mass of the paraxylene-rich product stream is less than 2.

3. The process of claim 1, further comprising isomerizing at least a portion of the first paraxylene-lean stream to form a secondary isomerate having a paraxylene concentration greater than the paraxylene concentration of the first paraxylene-lean stream.

4. The process of claim 3, wherein at least a portion of the secondary isomerate is used to form said C8-rich aromatic hydrocarbon mixture.

5. The process of claim 1, further comprising separating a feedstock containing aromatic hydrocarbons in a fractionation zone to form said C8-rich aromatic hydrocarbon mixture.

6. A process for the recovery of a paraxylene product from a mixture of C8 aromatic hydrocarbons, the process comprising:
    separating a C8-rich aromatic hydrocarbon mixture in a pressure swing adsorption zone to form a first paraxylene-rich stream and a first paraxylene-lean stream, wherein the first paraxylene-rich stream comprises less than 75 wt % paraxylene;
    separating at least a portion of the first paraxylene-rich stream in a crystallization zone to form a paraxylene-rich product stream and a second paraxylene-lean stream; wherein a ratio of the total mass of the second paraxylene-lean stream to the total mass of the paraxylene-rich product stream is less than 3; and
    isomerizing at least a portion of the second paraxylene-lean stream to form an isomerate having a paraxylene concentration greater than the paraxylene concentration of the second paraxylene-lean stream; wherein at least a portion of the isomerate is used to form said C8-rich aromatic hydrocarbon mixture.

7. The process of claim 6, wherein the ratio of the total mass of the second paraxylene-lean stream to the total mass of the paraxylene-rich product stream is less than 1.

8. The process of claim 6, further comprising isomerizing at least a portion of the first paraxylene-lean stream to form a secondary isomerate having a paraxylene concentration greater than the paraxylene concentration of the first paraxylene-lean stream.

9. The process of claim 8, wherein at least a portion of the secondary isomerate is used to form said C8-rich aromatic hydrocarbon mixture.

10. The process of claim 6, further comprising separating a feedstock containing aromatic hydrocarbons in a fractionation zone to form said C8-rich aromatic hydrocarbon mixture.

* * * * *